(12) United States Patent
Corbin et al.

(10) Patent No.: US 8,642,781 B2
(45) Date of Patent: Feb. 4, 2014

(54) PROCESS FOR THE NITRATION OF O-XYLENE AND RELATED COMPOUNDS

(75) Inventors: David Richard Corbin, West Chester, PA (US); Joachim C. Ritter, Wilmington, DE (US); James A. Schultz, Swedesboro, NJ (US); Sourav Kumar Sengupta, Wilmington, DE (US); Katelyn Rae Walck, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 137 days.

(21) Appl. No.: 12/870,188

(22) Filed: Aug. 27, 2010

(65) Prior Publication Data
US 2011/0054219 A1    Mar. 3, 2011

Related U.S. Application Data

(60) Provisional application No. 61/237,998, filed on Aug. 28, 2009.

(51) Int. Cl.
*C07C 209/00*   (2006.01)

(52) U.S. Cl.
USPC .......................................... 548/400; 564/411

(58) Field of Classification Search
None
See application file for complete search history.

(56) References Cited

U.S. PATENT DOCUMENTS

| | | | |
|---|---|---|---|
| 3,929,917 A | 12/1975 | Rauch | |
| 3,957,889 A * | 5/1976 | Milligan et al. | 568/937 |
| 3,965,200 A | 6/1976 | Manabe | |
| 3,966,830 A * | 6/1976 | Shimada et al. | 568/937 |
| 4,503,023 A | 3/1985 | Breck et al. | |
| 6,376,726 B1 | 4/2002 | Choudary | |
| 6,703,532 B2 | 3/2004 | Choudary | |
| 6,825,388 B2 * | 11/2004 | Dongare et al. | 568/940 |
| 2003/0166980 A1 | 9/2003 | Choudary | |
| 2004/0192977 A1 | 9/2004 | Dongare | |

FOREIGN PATENT DOCUMENTS

| | | |
|---|---|---|
| EP | 0949240 | 1/2003 |
| IN | 2001DE01308 | 7/2008 |
| JP | 47047370 | 11/1972 |
| WO | 00/51940 | 9/2000 |

OTHER PUBLICATIONS

Kantam, M. L., Choudary, B. M., Kumar, N. S., Ramprasad, K. V. Beta zeolite: an efficient and eco-friendly catalyst for the nitration of o-xylene with high regio-selectivity in liquid phase. J. Mol. Cata.—A: Chem. 2005, 229, 67-70.*
Fernandez-Bolanos, J., Overrend, W. G., Sykes, A., Tatlow, J. C., Wiseman, E. H., The synthesis of 4,5-bistnfluoromethylbenzimidazole. J. Chem. Soc. 1960, 4003-4010.*
Tsang, S. M., Paul, A. P., DiGiaimo, M. P. The nitration of toluene with alkyl nitrates and polyphosphoric acid. J. Org. Chem. 1964, 29, 3387-3390.*
Kantam, M. L., Rao, B. P. C., Choudary, B. M., Rao, K. K.,Sreedhar, B., Iwasawa,Y., Sasaki, T. Synthesis of nanocrystalline zeolite beta in supercritical fluids, characterization and catalytic activity. J. Mol. Catal.—A: Chem. 2006, 252, 76-84.*
Kantam, M. L Choudary, B. M., Kumar, N. S., Ramprasad, K. V. Beta zeolite: an efficient and eco-friendly catalyst for the nitration of o-xylene with high regio-selectivity in liquid phase. J. Mol. Cata.—A: Chem. 2005, 229, 67-70.*
Fernandez-Bolanos, J., Overrend, W. G., Sykes, A., Tatlow, J. C., Wiseman, E. H., The synthesis of 4,5-bistrifluoromethylbenzimidazole. J. Chem. Soc. 1960, 4003-4010.*
D'Angelo, J. Polyphosphoric Acid: What really is it. Review of the PPA workshop and recent studies. 2009, 1-35.*
B.M. Beglov, Investigation of the Process of the Thermal Dehydration of Orthophosphoric Acid in the Presence of Sulfuric and Nitric Acids, Zhurnal Prikladnoi Khimii, vol. 50, No. 2, pp. 460-463, Feb. 1977.
Robert A. Smiley, Phenylene- and Tolenediamines, pp. 1-6, 2005.
Reinoud J. Gaymans, Synthetic Methods in Step-Growth Polymers, Polyamides, p. 135-195, 2003.
John Dwyer and Alan Dyer, Zeolites for Industry, Chemistry & Industry, Apr. 2, 1984, pp. 237-245.
Fritz Blatter and Ernst Schumacher, The Preparation of Pure Zeolite NaY and its Conversion to High-Silica Faujasite, Journal of Chemical Education, vol. 67, No. 6, Jun. 1990, pp. 519-521.
Xi et al, Synthesis of 3,4-dimethylnitrobenzene by regioselective nitration with SO42-/ZrO2 supported on MCM-48 catalyst, Department of Biological and Chemical Engineering, Taizhou TechnicalCollege, Taizhou, 2006, 25 (12), pp. 1419-1422.
International Search Report, PCT/US2010/046900, Mar. 17, 2011.
Landau et al., Selectivity in Heterogeneous Catalytic Processes, Catalysis Today, 1997 (36) pp. 497-510.
Meshram et al., Clay Supported Ammonium Nitrate "Clayan", Synthetic Communications, 2003, V33 (14) pp. 2497-2498.
Patil et al., Regioselective nitration of O-Xylene, to 4-nitro-o-xylene Using Nitric Acid Over Solid Acid Catalysts, Catalysis Communications, 2003, (4), p. 429-434.
Shokrolahi et al., Wet Carbon-Based Solid Acid/NaNo3 as a Mild and Efficient Reagent for Nitration of Aromatic Compound Under Solvent Free Conditions, Chinese Chemical Letters, 2007 (18), p. 1064-066.
Smith et al., A Novel Method for the Nitration of Simple Aromatic Compounds, J. Org. Chem., 1998, (63), pp. 8448-8454.

* cited by examiner

*Primary Examiner* — Jason M Nolan
*Assistant Examiner* — Po-Chih Chen

(57) ABSTRACT

Aromatic compounds such as o-xylene are selectively nitrated by nitric acid in the presence of polyphosphoric acid and a large pore, acidic zeolite or a large pore, hydrophobic molecular sieve. This is an environmentally friendly, commercially viable, high conversion process for the selective nitration of aromatic compounds in the para position.

17 Claims, No Drawings

PROCESS FOR THE NITRATION OF O-XYLENE AND RELATED COMPOUNDS

This application claims priority under 35 U.S.C. §119(e) from, and claims the benefit of, U.S. Provisional Application No. 61/237,998, filed Aug. 28, 2009, which is by this reference incorporated in its entirety as a part hereof for all purposes.

TECHNICAL FIELD

This disclosure relates to a process for the nitration of aromatic compounds such as o-xylene to produce compounds that may be used as intermediates in the synthesis of a variety of industrial materials.

BACKGROUND

Nitration of aromatic compounds produces many large-volume chemicals such as nitrobenzene, nitrotoluenes, nitroxylenes, nitrochlorobenzenes and other nitroaromatics. Compounds such as these are important precursors and intermediates for aromatic diamines, explosives, dyes, pharmaceuticals, perfumes, pesticides, herbicides (such as pre-emergent herbicides), fiber systems, and many specialty chemicals.

Nitration of aromatic hydrocarbons has typically been carried out with a mixture of nitric and sulfuric acids in the liquid phase. However, the reactions are not very selective, which is particularly a problem if the para isomer is the more commercially desired isomer (e.g., if 4-nitro-o-xylene is more desired than 3-nitro-o-xylene). Conventional nitration processes often lead to over-nitration or to oxidized byproducts. In addition, aqueous work-up is often required, leading to the generation of large amounts of dilute aqueous acid waste streams, which cannot be recycled. This in turn, requires expensive and extensive separation and purification steps and disposal of waste.

In the past several decades, there have thus been concerted efforts in the agrichemical, specialties, and pharmaceutical industries to overcome such problems by developing cleaner, safer and/or more efficacious nitration processes. Such efforts have included processes that use, for example,

- mixed acids that contain sulfuric acid, acetic anhydride, polyphosphoric acid (as discussed in JP-B-47/047,370);
- solid acid catalysts such as zeolites (as discussed in Manoranjan et al, IN-A-2001DE01308); and
- solid superacid SO42-/ZrO$_2$ supported on mesoporous molecular sieve MCM-48 [as discussed in Xi et al, *Huagong Jinzhan*, 25(12), 1419-1422 (2006)].

U.S. Pat. No. 6,376,726 discloses a single acid process for preparing nitroaromatic compounds in which aromatic hydrocarbons are nitrated in the liquid phase using fuming nitric acid in the presence of a metal ion-exchanged clay catalyst, wherein the metal ion is $La^{3+}$, $Cu^{2+}$ or $Fe^{3+}$.

Unfortunately, processes such as those mentioned above are characterized by low conversion, low regioselectivity to 4-nitro-o-xylene, or the formation of large amounts of undesired byproduct, to a large enough extent and/or with a large enough frequency that their commercial value is diminished. In U.S. Pat. No. 6,376,726, for example, in the nitration of o-xylene in Example 10 (Table 3), the highest selectivity of 4-nitro-o-xylene over 3-nitro-o-xylene reported is 53 to 47 at a conversion of 56.8%.

A need thus remains for an environmentally friendly, commercially viable process for the selective nitration of aromatic compounds at high conversion.

SUMMARY

In one embodiment, this disclosure is directed to a process for the preparation of a nitrated product that is represented by the structure of the following Formula I:

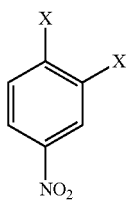

wherein each X is independently a $C_1$ to $C_{20}$ hydrocarbyl group, a halogen, a halogenated $C_1$ to $C_{20}$ hydrocarbyl group, a carboxylic acid group, or a nitrile group; comprising (a) contacting in a reaction mixture a substrate compound that is represented by the structure of the following Formula II:

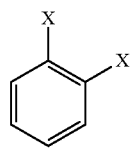

with polyphosphoric acid in the presence of a catalytic material selected from (i) a large pore, acidic zeolite having a molar ratio of Si/Al of greater than or equal to about 5, and (ii) a large pore, hydrophobic molecular sieve having a silicon content great than about 35 wt %; wherein the ratio of the weight of the catalytic material to the weight of the substrate compound is in the range of about 1/99 to about 25/75; and wherein X in Formula II is as set forth above for Formula I; and (b) adding nitric acid to the reaction mixture to provide therein (i) a molar ratio of nitric acid to substrate compound (on a 100% nitric acid basis) in the range of about 1/1 to about 1/1.5, and (ii) a weight ratio of nitric acid to polyphosphoric acid in the range of about 15/85 to about 40/60, to form a nitrated product.

In an alternative embodiment, the processes hereof include a process for the preparation of a nitrated product that is represented by the structure of the following Formula I(a):

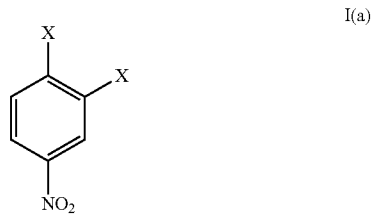

wherein the two Xs are not equal, and each X is independently a $C_1$ to $C_{20}$ hydrocarbyl group, a halogen, a halogenated $C_1$ to $C_{20}$ hydrocarbyl group, a carboxylic acid group, or a nitrile group; by (a) contacting in a reaction mixture a substrate compound that is represented by the structure of the following Formula III:

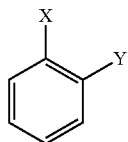

with polyphosphoric acid in the presence of a catalytic material selected from (i) a large pore, acidic zeolite having a molar ratio of Si/Al of greater than or equal to about 5, and (ii) a large pore, hydrophobic molecular sieve having a silicon content great than about 35 wt %; wherein the ratio of the weight of the catalytic material to the weight of the substrate compound is in the range of about 1/99 to about 25/75; and wherein X and Y in Formula III represent the two unequal Xs as set forth above for Formula I(a); and (b) adding nitric acid to the reaction mixture to provide therein (i) a molar ratio of nitric acid to substrate compound (on a 100% nitric acid basis) in the range of about 1/1 to about 1/1.5, and (ii) a weight ratio of nitric acid to polyphosphoric acid in the range of about 15/85 to about 40/60, to form a nitrated product.

DETAILED DESCRIPTION

One embodiment of the processes hereof is directed to a process for the preparation of a nitrated product that is represented by the structure of the following Formula I:

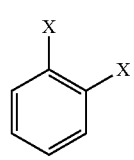

wherein each X is independently a $C_1$ to $C_{20}$ hydrocarbyl group, a halogen, a halogenated $C_1$ to $C_{20}$ hydrocarbyl group, a carboxylic acid group, or a nitrile group; by (a) contacting in a reaction mixture a substrate compound that is represented by the structure of the following Formula II:

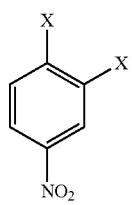

with polyphosphoric acid in the presence of a catalytic material selected from (i) a large pore, acidic zeolite having a molar ratio of Si/Al of greater than or equal to about 5, and (ii) a large pore, hydrophobic molecular sieve having a silicon content great than about 35 wt %; wherein the ratio of the weight of the catalytic material to the weight of the substrate compound is in the range of about 1/99 to about 25/75; and wherein X in Formula II is as set forth above for Formula I; and (b) adding nitric acid to the reaction mixture to provide therein (i) a molar ratio of nitric acid to substrate compound (on a 100% nitric acid basis) in the range of about 1/1 to about 1/1.5, and (ii) a weight ratio of nitric acid to polyphosphoric acid in the range of about 15/85 to about 40/60, to form a nitrated product.

A $C_1$ to $C_{20}$ hydrocarbyl group, as referred to above in connection with Formula I, is a univalent radical containing only carbon and hydrogen that is inert to the reaction and does not interfere with the operation of the catalyst. A halogenated hydrocarbyl group is a hydrocarbyl group that contains one or more halogen atoms (such as F, Cl, Br or I). In one embodiment hereof, X is a $C_1$ to $C_{12}$ hydrocarbyl group, or a $C_1$ to $C_{10}$ hydrocarbyl group, or a $C_1$ to $C_8$ hydrocarbyl group, or a $C_1$ to $C_6$ hydrocarbyl group. In another embodiment hereof, X is $CH_3$. In yet another embodiment hereof, X is a $C_2$, $C_3$, $C_4$, $C_5$, $C_6$, $C_7$, $C_8$, $C_9$, $C_{10}$, $C_{11}$ or $C_{12}$ hydrocarbyl group. In yet another embodiment hereof, X is a fluorinated, chlorinated or brominated $C_1$ to $C_{12}$, $C_1$ to $C_{10}$, $C_1$ to $C_8$, or $C_1$ to $C_6$ hydrocarbyl group, such as a fluorinated methyl, ethyl, propyl or butyl group.

In a first step of a process hereof, the substrate compound (o-xylene or a derivative thereof) is contacted with polyphosphoric acid ("PPA") in the presence of catalytic material. Polyphosphoric acid refers to the compound:

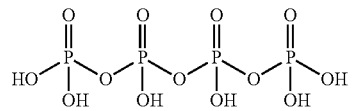 [SMILES: O=P(O)(O)OP(=O)(O)OP(=O)(O)OP(=O)(O)O]

Polyphosphoric acid is available commercially in two different compositions: 105% and 115%. The percent value of polyphosphoric acid refers to its content of $H_3PO_4$ (i.e. 100 grams of the 115% PPA contains 115 grams of $H_3PO_4$, while 100 grams of the 105% PPA has 105 grams of $H_3PO_4$). PPA may be used in a process hereof in either the 105% or the 115% strength.

The catalytic material in the presence of which the substrate compound is contacted with PPA may be either or both of (i) a large pore, acidic zeolite having a Si/Al ratio greater than or equal to about 5, or (ii) a large pore, hydrophobic molecular sieve having a silicon content great than about 35 wt %. Acting as a catalyst, the catalytic material would not participate in the reaction in any manner in which it would be chemically altered, but it is believed nevertheless to modify one or more parameters of the reaction to thereby enhance product formation.

The catalytic material is typically used in a weight amount ranging from about 1% to about 25% of the combined weight of the catalytic material plus the substrate compound. That is, the ratio of the weight of the catalytic material to the weight of the substrate compound is in the range of about 1/99 to about 25/75. In another embodiment, catalytic material is used in a weight amount ranging from about 5% to about 20% of the combined weight of catalytic material plus substrate compound, which may also be expressed as a weight ratio of about 5/95 to about 20/80.

Zeolites suitable for use as a catalyst herein can be generally represented by the following formula $M_{2/n}O \cdot Al_2O_3 \cdot xSiO_2 \cdot yH_2O$ wherein M is a cation of valence n, x is greater than or equal to about 2, and y is a number determined by the porosity and the hydration state of the zeolite, generally from about 2 to about 8. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

The zeolite framework structure has corner-linked tetrahedra with Al or Si atoms at centers of the tetrahedra and oxygen atoms at the corners. Such tetrahedra are combined in a well-defined repeating structure comprising various combinations of 4-, 6-, 8-, 10-, and 12-membered rings. The resulting framework structure is pore network of regular channels and cages that is useful for separation. Pore dimensions are determined by the geometry of the aluminosilicate tetrahedra forming the zeolite channels or cages, with nominal openings of about 0.26 nm for 6-member rings, about 0.40 nm for 8-member rings, about 0.55 nm for 10-member rings, and about 0.74 nm for 12-member rings (these numbers assume the ionic radii for oxygen). Zeolites with the largest pores, being 8-member rings, 10-member rings, and 12-member rings, are frequently considered small, medium and large pore zeolites, respectively. In a zeolite, the term "silicon to aluminum ratio" or, equivalently, "Si/Al ratio" means the ratio of silicon atoms to aluminum atoms.

Pore dimensions are critical to the performance of these materials in catalytic and separation applications, since this characteristic determines whether molecules of a certain size can enter and exit the zeolite framework. In practice, it has been observed that very slight decreases in ring dimensions can effectively hinder or block movement of particular molecular species through the zeolite structure.

The effective pore dimensions that control access to the interior of the zeolites are determined not only by the geometric dimensions of the tetrahedra forming the pore opening, but also by the presence or absence of ions in or near the pore. For example, in the case of zeolite type A, access can be restricted by monovalent ions, such as $Na^+$ or $K^+$, which are situated in or near 8-member ring openings as well as 6-member ring openings. Access can be enhanced by divalent ions, such as $Ca^{2+}$, which are situated only in or near 6-member ring openings. Thus, the potassium and sodium salts of zeolite A exhibit effective pore openings of about 0.3 nm and about 0.4 nm, respectively, whereas the calcium salt of zeolite A has an effective pore opening of about 0.5 nm. The presence or absence of ions in or near the pores, channels and/or cages can also significantly modify the accessible pore volume of the zeolite for sorbing materials.

Representative examples of zeolites suitable for use herein include (i) small pore zeolites such as NaA (LTA), CaA (LTA), Erionite (ERI), Rho (RHO), ZK-5 (KFI) and chabazite (CHA); (ii) medium pore zeolites such as ZSM-5 (MFI), ZSM-11 (MEL), ZSM-22 (TON), and ZSM-48; and (iii) large pore zeolites such as zeolite beta (BEA), faujasite (FAU), mordenite (MOR), zeolite L (LTL), NaX (FAU), NaY (FAU), DA-Y (FAU) and CaY (FAU). The letters in parentheses give the framework structure type of the zeolite.

Zeolites suitable for use herein also include large pore, acidic, hydrophobic zeolites, including without limitation faujasites, beta, and mordenite zeolites, having a high silicon to aluminum ratio. Large pore zeolites have a framework structure consisting of 12 membered rings with a pore size of about 0.65 to about 0.75 nm. Hydrophobic zeolites generally have Si/Al ratios greater than or equal to about 5, and the hydrophobicity generally increases with increasing Si/Al ratios.

Zeolites with a high Si/Al ratio can be prepared synthetically, or by modification of high alumina-containing zeolites using methods known in the art. These methods include without limitation treatment with $SiCl_4$ or $(NH_4)_2SiF_6$ to replace Al with Si, as well as treatment with steam followed by acid. For example, a $SiCl_4$ treatment suitable for such purpose is described by Blatter [*J. Chem. Ed.* 67 (1990) 519]. A $(NH_4)_2SiF_6$ treatment suitable for such purpose is described in U.S. Pat. No. 4,503,023. These treatments are generally very effective at increasing the Si/Al ratio for zeolites such as zeolites Y and mordenite. In addition, WO 00/51940 describes a method for preparing a zeolite with a high Si/Al ratio by calcining a zeolite in steam under turbulent conditions with respect to the flow pattern of the zeolite at a temperature between 650 and 1000° C. The presence of aluminum atoms in the frameworks results in hydrophilic sites. On removal of these framework aluminum atoms, water adsorption is seen to decrease and the material becomes more hydrophobic and generally more organophilic. Hydrophobic properties in zeolites are discussed further by Chen [*J. Phys. Chem.* 80 (1976) 60]. Generally, high Si/Al containing zeolites exhibit higher thermal and acid stability.

Acid forms of zeolites can be prepared by a variety of techniques including ammonium exchange followed by calcination, or by direct exchange of alkali ions for protons using mineral acids or ion exchangers. Acid forms of zeolites are discussed further in Dwyer, "Zeolite, Structure, Composition and Catalysis" in *Chemistry and Industry*, Apr. 2, 1984.

Certain types of molecular sieves, of which zeolites are a sub-type, may also be used as the catalytic material in the processes hereof. While zeolites are aluminosilicates, molecular sieves contain other elements in place of aluminum and silicon, but have analogous structures. Large pore, hydrophobic molecular sieves that have similar properties to the preferred zeolites described above are suitable for use herein. Examples of such molecular sieves include without limitation Ti-Beta, B-Beta, and Ga-Beta silicates. Molecular sieves are discussed further in Szostak, *Molecular Sieves Principles of Synthesis and Identification*, (Van Nostrand Reinhold, NY, 1989).

After contacting the substrate compound with PPA in the reaction mixture in the presence of the catalytic material, nitric acid is added to the reaction mixture to provide therein (i) a molar ratio of nitric acid to substrate compound (on a 100% nitric acid basis) in the range of about 1/1 to about 1/1.5, and (ii) a weight ratio of nitric acid to polyphosphoric acid in the range of about 15/85 to about 40/60. In an alternative embodiment, the molar ratio of nitric acid to substrate compound (on a 100% nitric acid basis) may be in the range of about 1/1 to about 1/1.2. The amount of nitric acid added to the reaction mixture is calculated on the basis of 100% nitric acid [i.e. 100 wt % concentration (anhydrous) nitric acid], but the nitric acid that is actually added to the reaction mixture may be a nitric acid having a strength (wt % concentration) in the range of about 70% strength to about 100% strength. In a further alternative embodiment, the weight ratio of nitric acid to polyphosphoric acid may be in the range of about 20/80 to about 25/75.

In a further alternative embodiment, nitric acid may be co-fed to the reaction mixture together with a nitro compound as a diluent. A nitro compound used as a diluent herein is an organic compound that contains one or more nitro functional groups ($-NO_2$). The nitric acid and diluent may be fed to the reaction mixture in the same or separate streams. Examples of nitro compounds suitable for use as diluent include without limitation nitrobenzene and nitromethane. The mole ratio of diluent to substrate may be in the range of about 0 to about 5, and in one particular embodiment it is in the range of about 0.5 to about 1. The nitric acid, or nitric acid/diluent mixture, is added gradually to the reaction mixture.

The temperature of the reaction mixture may be adjusted before and/or after the addition of nitric acid thereto by heating or cooling, usually heating. The temperature of the reaction mixture may be adjusted on either or both occasions to a temperature that is expressed in terms of any of the possible ranges that may be formed from a combination of any two of the following maxima and minima: where the minim are about 0° C. or more, or about 10° C. or more, or about 20° C. or more, or about 30° C. or more, or about 40° C. or more, or about 45° C. or more, and yet where the maxima are about 100° C. or less, or about 90° C. or less, or about 80° C. or less, or about 70° C. or less, or about 60° C. or less, or about 55° C. or less. In various alternative embodiments, the temperature may be adjusted to a temperature that is, for example, in the range of about 0° C. or more and about 100° C. or less; or in the range of about 10° C. or more and about 60° C. or less; or in the range of about 20° C. or more and about 70° C. or less; or in the range of about 30° C. or more and about 80° C. or less; or in the range of about 40° C. or more and about 90° C. or less.

Either before and/or after the addition of nitric acid, or both occasions, the temperature of the reaction mixture, once adjusted to the desired level, may be maintained at that level for a time period that is in the range of about 2 hours to about 24 hours or about 4 hours to about 10 hours. In a further alternative embodiment, the temperature of the reaction mixture may be held at a desired level until the reaction reaches a steady state; and in a further alternative embodiment, the reaction mixture may be heated to a temperature between about 45° C. and about 55° C. for about 1 hour after nitric acid addition is complete.

The reaction product, the nitrated product, may optionally then be isolated and/or recovered by any appropriate means known in the art. In one embodiment, the reaction mixture is quenched with cold water and the nitrated product is isolated by solvent extraction. Examples of solvents suitable for use for such purpose include without limitation methylene chloride. In another embodiment, the hot reaction mixture is filtered neat to remove catalyst. Two phases are evident, and the top (product) layer is decanted away, washed with water and base, and dried.

One illustrative embodiment of the processes hereof, when the substrate is o-xylene (i.e. $X=CH_3$) and the catalytic material is the zeolite CBV-30A, is shown schematically below:

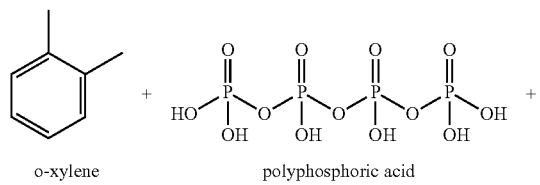

o-xylene   polyphosphoric acid

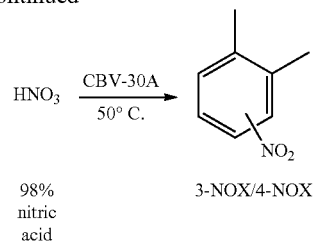

98% nitric acid   3-NOX/4-NOX

The terms "3-NOX" and "4-NOX" refer, respectively, to 3-nitro-o-xylene and 4-nitro-o-xylene, as represented by the structures shown below:

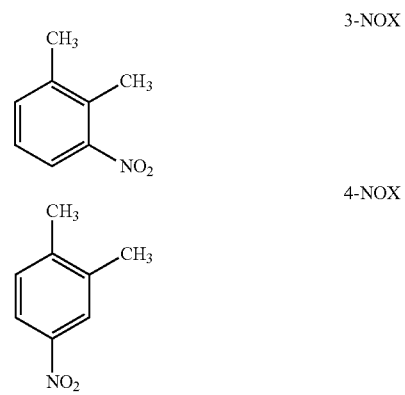

The processes hereof provide higher conversion, better selectivity (i.e. selective nitration) to para isomers (e.g. 4-NOX), and little or no oxidation products or other undesired byproducts compared to conventional processes. The use of a zeolite catalyst or molecular sieve catalyst in conjunction with polyphosphoric acid, without the use of sulfuric acid as in conventional process, makes the process environmentally friendly, safe, and economical because the catalyst and polyphosphoric acid can be recycled and reused many times. Moreover, in one particular embodiment hereof, the processes hereof may be run in the absence of sulfuric acid. The dehydration of PPA is further discussed in Dzhuraev et al, *Doklady Akademii Nauk USSR* 7 (1976) 39-40; and in Beglov et al, *Zhurnal Prikladnoi Khimii* (Sankt-Peterburg, Russian Federation) 50(2) (1977) 460-463.

In an alternative embodiment, the processes hereof include a process for the preparation of a nitrated product that is represented by the structure of the following Formula I(a):

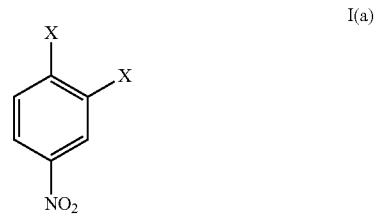

wherein the two Xs are not equal, and each X is independently a $C_1$ to $C_{20}$ hydrocarbyl group, a halogen, a halogenated $C_1$ to $C_{20}$ hydrocarbyl group, a carboxylic acid group, or a nitrile group; by (a) contacting in a reaction mixture a substrate compound that is represented by the structure of the following Formula III:

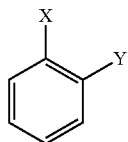

with polyphosphoric acid in the presence of a catalytic material selected from (i) a large pore, acidic zeolite having a molar ratio of Si/Al of greater than or equal to about 5, and (ii) a large pore, hydrophobic molecular sieve having a silicon content great than about 35 wt %; wherein the ratio of the weight of the catalytic material to the weight of the substrate compound is in the range of about 1/99 to about 25/75; and wherein X and Y in Formula III represent the two unequal Xs as set forth above for Formula I(a); and (b) adding nitric acid to the reaction mixture to provide therein (i) a molar ratio of nitric acid to substrate compound (on a 100% nitric acid basis) in the range of about 1/1 to about 1/1.5, and (ii) a weight ratio of nitric acid to polyphosphoric acid in the range of about 15/85 to about 40/60, to form a nitrated product.

In the reaction in which the compound of Formula III is used as the substrate compound, the nitrated product will be selectively nitrated at the position para to the X or Y substituent that has the greater o,p-directing power. The same process characteristics as described above also apply to the reaction in which the compound of Formula III is used as the substrate compound.

The process described herein can be used for the selective synthesis of p-dinitrobenzene, which in turn can be hydrogenated to produce p-phenylene diamine (PPD), which is used to manufacture poly(p-phenylene terephthalamide). The processes can also be used to make m-dinitrobenzene, which can be hydrogenated to produce m-phenylene diamine (MPD), which is used to manufacture poly(m-phenylene terephthalamide). MPD is an important intermediate in the production of aramid fibers.

EXAMPLES

The operation and effects of certain embodiments of the inventions hereof may be more fully appreciated from a series of examples (Examples 1-11), as described below. The embodiments on which these examples are based are representative only, and the selection of those embodiments to illustrate the invention does not indicate that materials, components, reactants, conditions or protocols not described in the examples are not suitable for use herein, or that subject matter not described in the examples is excluded from the scope of the appended claims and equivalents thereof. The significance of the examples is better understood by comparing the results obtained therefrom with the results obtained from a trial run that is designed to serve as a controlled experiment (Comparative Example A) and illustrate the results obtained when ytterbium trifluoromethanesulfonate is used as the catalyst instead of a zeolite or molecular sieve.

The meaning of abbreviations is as follows: "4-NOX" means 4-nitro-o-xylene, "DI" means deionized, "eq" means equivalent(s), "g" means gram(s), "GC" means gas chromatography, "h" means hour(s), "HPLC" means high pressure liquid chromatography, "mL" means milliliter(s), "MS" means mass spectrometry, and "Yb(Otf)$_3$" means ytterbium trifluoromethanesulfonate.

Analysis

Samples from the nitration mass were analyzed by GC/MS and HPLC/MS. Conversion and selectivity for 4-NOX are reported as mole percents. GC response factors were not assigned for by-product dinitration compounds, and those amounts are instead reported as area percents, referring to the observed GC area percent for those compounds.

The process hereof advantageously provides an increased selectivity to, and yield of, the desired nitrated product as compared to known processes. As used herein, the term "selectivity" for a product ("P") denotes the molar fraction or molar percentage of P in the final product mix, and the term "conversion" denotes how much reactant was used up as a fraction or percentage of the theoretical amount. The conversion multiplied by the selectivity thus equals the maximum "yield" of P, while the actual yield, also referred to as "net yield," will normally be somewhat less than this because of sample losses incurred in the course of activities such as isolating, handling, drying, and the like. As used herein, the term "purity" denotes what percentage of the in-hand, isolated sample is actually the specified substance.

Materials

The zeolites were obtained from Zeolyst Corp (Conshohocken, Pennsylvania, USA). They were calcined using the following procedure: In air, heat from room temperature to 475° C. at a rate of 25° C./min; hold 10 minutes at 475° C., then heat at 12.5° C./min to 525 deg C.; hold at 525° C. for 10 minutes, then heat at 1° C./min to 550° C.; hold at 550° C. for 8 hours, then cool at 20° C./min to 110° C.; hold until turned off. The sample is transferred to dry containers at 110° C.

115% Polyphosphoric acid, o-xylene (97% purity), and ytterbium trifluoromethanesulfonate (99.99% purity) were obtained from Sigma-Aldrich (Milwaukee, Wis., USA) and used as received.

Example 1

A reaction mixture was prepared by combining 12.7 g (0.12 mol, 1.2 eq) of o-xylene, 2 g of catalyst (CBV-780) Si/Al ratio=40, and 30 g of 115% polyphosphoric acid in a dry, 100 mL round bottom flask as a reactor, and was stirred mechanically while being heated to 50° C. Separately, 6.3 g (0.1 mol, 1 eq) of 100% nitric acid was combined and homogenized with 10 g nitrobenzene in an addition funnel. After the reaction mixture attained steady state, the nitric acid/nitrobenzene mixture was added drop-wise at 50° C., keeping the reactor temperature below 60° C. The reactor was held at 50° C. for 1 h after the completion of the addition of nitric acid/nitrobenzene mixture.

The reaction mixture was then quenched with 40 mL of cold DI water and stirred vigorously. Next, approximately 30 mL of methylene chloride was added to the reactor and stirred. The contents of the reactor were filtered through celite and rinsed with DI water and methylene chloride until the filtrate was colorless. The filtrate was transferred into a separation funnel and phase cut was carried out. The aqueous layer was extracted once more with methylene chloride and the combined organic layer was dried over magnesium sulfate. The organic layer containing magnesium sulfate was filtered and methylene chloride was removed in a rotovap.

Final weight was recorded to determine overall yield. Samples from the nitration mass were analyzed by GC/MS and HPLC/MS. Conversion was 85.4 mol %, the selectivity for 4-NOX) was 71.0 mol %, and the by-product proportion was 9.8 area %.

Example 2

A reaction mixture was prepared by combining 10 g (0.1 mol) of o-xylene, 10 g (0.08 mol) of nitrobenzene, 1 g of Hydrogen Y zeolite catalyst [CBV-780, Si/Al=40], and 25 g of 115% polyphosphoric acid in a dry, 100 mL round bottom flask as a reactor, and was stirred mechanically. Separately, 4.23 g (0.07 mol) of 98% nitric acid was slowly added over 2 h via an addition funnel at 25° C. A temperature exotherm to 32° C. was observed upon addition of nitric acid. The reactor was held at 25° C. for 24 h. The reaction mixture was then quenched with 40 mL of cold DI water and stirred vigorously.

Next, approximately 30 mL of methylene chloride was added to the reactor and stirred. The contents of the reactor were filtered through celite and rinsed with DI water and methylene chloride until the filtrate was colorless. The filtrate was transferred into a separation funnel and phase cut was carried out. The aqueous layer was extracted once more with methylene chloride and the combined organic layer was dried over magnesium sulfate. The organic layer containing magnesium sulfate was filtered and methylene chloride was removed in a rotovap.

g of 115% polyphosphoric acid in a dry, 15 mL vial as a reactor, and was stirred magnetically. Separately, 0.61 g (0.01 mol) of 98% nitric acid was added. The reaction mixture was held at 25° C. for 24 h, then heated to 50° C. for 2 h. The reaction mixture was then quenched with 5 mL of cold DI water and stirred vigorously.

Next, approximately 3 mL of methylene chloride was added to the reactor and stirred. The contents of the reactor were filtered through celite and rinsed with DI water and methylene chloride until the filtrate was colorless. The filtrate was transferred into a separation funnel and phase cut was carried out. The aqueous layer was extracted once more with methylene chloride and the combined organic layer was dried over magnesium sulfate. The organic layer containing magnesium sulfate was filtered and methylene chloride was removed in a rotovap.

Final weight was recorded to determine overall yield. Samples from the nitration mass were analyzed by GC/MS. Results are presented in Table 1.

The above procedure was repeated for Comparative Example A, except that the catalyst was not a zeolite or molecular sieve but a different acidic inorganic material, ytterbium trifluoromethanesulfonate. Results are presented in Table 1. While high conversion and low byproduct formation were observed with this catalyst, selectivity to 4-NOX was only 48.0%.

TABLE 1

| EXAMPLE | CATALYST DESIGNATION | CATALYST IDENTITY | CONVERSION (MOL %) | SELECTIVITY (MOL %) | BYPRODUCT (AREA %) |
|---|---|---|---|---|---|
| 3 | CP-811C-300B | Hydrogen-beta Zeolite Si/Al = 175 | 90.8 | 69.5 | 7.2 |
| 4 | CBV-90A | Hydrogen-Mordenite Zeolite Si/Al = 45 | 87.7 | 58.2 | 3.0 |
| 5 | CBV-30A | Hydrogen-Mordenite Zeolite Si/Al = 15 | 90.7 | 63.4 | 8.9 |
| 6 | CBV-30A | Hydrogen-Mordenite Zeolite Si/Al = 15 | 95.8 | 62.3 | 1.4 |
| 7 | CBV-780 | Hydrogen Y Zeolite Si/Al = 40 | 99.1 | 68.8 | 7.0 |
| 8 | CBV-760 | Hydrogen Y Zeolite Si/Al = 30 | 94.1 | 61.6 | 4.2 |
| 9 | CBV-90A | Hydrogen-Mordenite Zeolite Si/Al = 45 | 87.5 | 65.8 | 5.9 |
| Comparative Example A | Yb(Otf)$_3$ | Yb(Otf)$_3$ | 100.0 | 48.0 | 1.1 |

Final weight was recorded to determine overall yield. Samples from the nitration mass were analyzed by GC/MS. Conversion was 62.0 mol %, the selectivity (4-NOX) was 76.6 mol %, and the by-product proportion was 14.4 area %.

Examples 3-9, Comparative Example A

For Examples 3-9, a reaction mixture was prepared by combining 1 g (0.01 mol) of o-xylene, 1.4 g (0.01 mol) of nitrobenzene, 1 g of zeolite catalyst (see chart below), and 2

Example 10

A reaction mixture was prepared by combining 12.7 g (0.12 mol) of o-xylene, 2 g of H-mordenite zeolite catalyst [CBV-30A, Si/Al=15], and 25 g of 115% polyphosphoric acid in a dry, 100 mL round bottom flask as a reactor, and was stirred mechanically while being heated to 50° C. Separately, 6.3 g (0.1 mol) of 98% nitric acid was added via an addition funnel, slowly at 50° C. The reaction was carried out at 50° C. and was held at 50° C. for 1 h after the completion of the addition of nitric acid.

The reaction mixture was then quenched with 40 mL of cold DI water and stirred vigorously. Next, approximately 30 mL of methylene chloride was added to the reactor and stirred. The contents of the reactor were filtered through celite and rinsed with DI water and methylene chloride until the filtrate was colorless. The filtrate was transferred into a separation funnel and phase cut was carried out. The aqueous layer was extracted once more with methylene chloride and the combined organic layer was dried over magnesium sulfate. The organic layer containing magnesium sulfate was filtered and methylene chloride was removed in a rotovap.

Final weight was recorded to determine overall yield. Samples from the nitration mass were analyzed by GC/MS. Conversion was 87.4 mol %, the, selectivity (4-NOX) was 66.7 mol %, and the by-product proportion was 21.44 area %.

Example 11

A reaction mixture was prepared by combining 12.7 g (0.12 mol) of o-xylene, 5 g (0.08 mol) of nitromethane, 2 g of [CP814C-beta Si/Al=19], and 30 g of 115% polyphosphoric acid in a dry, 100 mL round bottom flask as a reactor, and was stirred mechanically while being heated to 50° C. Separately, 7.0 g (0.11 mol) of 100% nitric acid were added via a syringe pump (Sono-Tek Model 12-05124) at a rate of 1 mL/hour at 50° C. The reaction was carried out at 50° C. and the reactor was held at 50° C. for 24 h. The reaction mixture was then quenched with 40 mL of cold DI water and stirred vigorously.

Next, approximately 30 mL of methylene chloride was added to the reactor and stirred. The contents of the reactor were filtered through celite and rinsed with DI water and methylene chloride until the filtrate was colorless. The filtrate was transferred into a separation funnel and phase cut was carried out. The aqueous layer was extracted once more with methylene chloride and the combined organic layer was dried over magnesium sulfate. The organic layer containing magnesium sulfate was filtered and methylene chloride was removed in a rotovap.

Final weight was recorded to determine overall yield. Samples from the nitration mass were analyzed by GC/MS. Conversion was 90.8 mol %, the selectivity (4-NOX) was 58.7 mol %, and the by-product proportion was 11.18 area %.

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, (a) amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value; (b) use of the indefinite article "a" or "an" with respect to a statement or description of the presence of an element or feature of this invention, does not limit the presence of the element or feature to one in number; and (c) the words "include", "includes" and "including" are to be read and interpreted as if they were followed by the phrase "without limitation" if in fact that is not the case.

What is claimed is:
1. A process for the preparation of a nitrated product that is represented by the structure of the following Formula I:

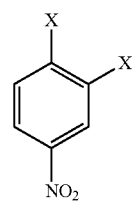

wherein the two Xs are not equal, and each X is independently a $C_1$ to $C_{20}$ hydrocarbyl group, a halogenated $C_1$ to $C_{20}$ hydrocarbyl group, a carboxylic acid group, or a nitrile group; comprising
  (a) contacting in a reaction mixture a substrate compound that is represented by the structure of the following Formula II:

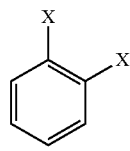

with polyphosphoric acid in the presence of a catalytic material selected from (i) a large pore, acidic zeolite having a molar ratio of Si/Al of greater than or equal to about 5, or (ii) a large pore, hydrophobic molecular sieve having a silicon content great than about 35 wt %; wherein the ratio of the weight of the catalytic material to the weight of the substrate compound is in the range of about 1/99 to about 25/75; and wherein X in Formula II is as set forth above for Formula I; and (b) adding nitric acid to the reaction mixture to provide therein (i) a molar ratio of nitric acid to substrate compound (on a 100% nitric acid basis) in the range of about 1/1 to about 1/1.5, and (ii) a weight ratio of nitric acid to polyphosphoric acid in the range of about 15/85 to about 40/60, to form a nitrated product of formula I.

2. A process according to claim 1 wherein a $C_1$ to $C_{20}$ hydrocarbyl group is $CH_3$.

3. A process according to claim 1 wherein a halogenated $C_1$ to $C_{20}$ hydrocarbyl group is a fluorinated alkyl group.

4. A process according to claim 1 wherein a zeolite is selected from the members of the group consisting of faujasite, mordenite, beta, EMT, ITQ-21, ITQ-4, and SSZ-31.

5. A process according to claim 1 wherein a molecular sieve is selected from the members of the group consisting of Ti-Beta silicate, B-Beta silicate, and Ga-Beta silicate.

6. A process according to claim 1 wherein the weight ratio of catalytic material to substrate compound is in the range of about 5/95 to about 20/80.

7. A process according to claim 1 wherein the polyphosphoric acid is 115% polyphosphoric acid.

8. A process according to claim 1 wherein the molar ratio of nitric acid to substrate compound is in the range of about 1/1 to about 1/1.2.

9. A process according to claim 1 wherein the weight ratio of nitric acid to polyphosphoric acid is in the range of about 20/80 to about 25/75.

10. A process according to claim 1 further comprising a step (a-1) of adjusting the temperature of the reaction mixture before the addition of nitric acid.

11. A process according to claim 1 further comprising a step (c-1) of adjusting the temperature of the reaction mixture after the addition of nitric acid.

12. A process according to claim 1 further comprising addition with the nitric acid and a nitro compound diluent.

13. A process according to claim 12 wherein the diluent is selected from one or both of nitrobenzene and nitromethane.

14. A process according to claim 12 wherein the nitric acid and diluent are co-fed in separate streams.

15. A process according to claim 12 wherein the molar ratio of diluent to substrate compound is less than about 5/1.

16. A process according to claim 12 wherein the molar ratio of diluent to substrate compound is in the range of about 0.5/1 to about 1/1.

17. A process according to claim 1 further comprising a step (c-2) of isolating and/or recovering the nitrated product of formula I.

* * * * *